US009149664B2

(12) United States Patent
Davis et al.

(10) Patent No.: US 9,149,664 B2
(45) Date of Patent: Oct. 6, 2015

(54) SUNSCREEN COMPOSITIONS

(75) Inventors: Jennifer Davis, Ewing, NJ (US);
Doreen Petersen, Princeton, NJ (US)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 11/955,346

(22) Filed: Dec. 12, 2007

(65) Prior Publication Data
US 2008/0181858 A1    Jul. 31, 2008

Related U.S. Application Data

(60) Provisional application No. 60/887,370, filed on Jan. 31, 2007, provisional application No. 60/951,090, filed on Jul. 20, 2007, provisional application No. 60/987,948, filed on Nov. 14, 2007.

(51) Int. Cl.
*A61K 8/29* (2006.01)
*A61K 8/27* (2006.01)
*A61K 8/30* (2006.01)
*A61Q 17/04* (2006.01)
*A61K 8/73* (2006.01)
*A61K 8/81* (2006.01)
*A61K 8/87* (2006.01)

(52) U.S. Cl.
CPC . *A61Q 17/04* (2013.01); *A61K 8/73* (2013.01); *A61K 8/8147* (2013.01); *A61K 8/8152* (2013.01); *A61K 8/8158* (2013.01); *A61K 8/87* (2013.01)

(58) Field of Classification Search
USPC ............................ 424/59, 60, 78.08, 400, 401
See application file for complete search history.

(56) References Cited

U.S. PATENT DOCUMENTS

| | | | |
|---|---|---|---|
| 3,349,077 A | 10/1967 | Schweiger | |
| 4,209,729 A | 6/1980 | McElroy | |
| 4,465,702 A | 8/1984 | Eastman et al. | |
| 4,477,480 A | 10/1984 | Seidel et al. | |
| 4,591,610 A | 5/1986 | Grollier | |
| 4,595,586 A * | 6/1986 | Flom | 424/59 |
| 4,667,026 A | 5/1987 | Jarry et al. | |
| 4,879,367 A | 11/1989 | Piejko et al. | |
| 5,037,929 A | 8/1991 | Rajagopalan et al. | |
| 5,131,953 A | 7/1992 | Kasica et al. | |
| 5,149,799 A | 9/1992 | Rubens | |
| 5,187,272 A | 2/1993 | Katcher et al. | |
| 5,198,469 A | 3/1993 | Sakata | |
| 5,508,055 A | 4/1996 | Rubow et al. | |
| 5,538,720 A | 7/1996 | Jendryssek-Pfaff et al. | |
| 5,593,503 A | 1/1997 | Shi et al. | |
| 5,679,556 A | 10/1997 | Homma et al. | |
| 5,753,215 A | 5/1998 | Mougin et al. | |
| 6,017,860 A | 1/2000 | Sajic et al. | |
| 6,090,375 A | 7/2000 | Rechelbacher et al. | |
| 6,113,881 A | 9/2000 | Bhatt et al. | |
| 6,147,038 A | 11/2000 | Halloran | |
| 6,180,122 B1 | 1/2001 | Roulier et al. | |
| 6,218,346 B1 | 4/2001 | Sajic et al. | |
| 6,531,118 B1 * | 3/2003 | Gonzalez et al. | 424/59 |
| 6,716,418 B2 | 4/2004 | SenGupta et al. | |
| 6,887,400 B1 * | 5/2005 | Wei et al. | 252/405 |
| 7,014,842 B2 | 3/2006 | Dueva-Koganove et al. | |
| 2003/0049290 A1 * | 3/2003 | Jha et al. | 424/401 |
| 2003/0108505 A1 | 6/2003 | Cao et al. | |
| 2003/0143179 A1 * | 7/2003 | Cao et al. | 424/70.13 |
| 2003/0228267 A1 | 12/2003 | Aust et al. | |
| 2004/0234486 A1 | 11/2004 | Hashimoto | |
| 2005/0112080 A1 | 5/2005 | Cao et al. | |
| 2006/0013785 A1 | 1/2006 | Lauscher et al. | |

FOREIGN PATENT DOCUMENTS

| | | |
|---|---|---|
| EP | 0 180 366 B1 | 5/1986 |
| EP | 0 321 216 A2 | 6/1989 |
| EP | 0 412 705 B1 | 2/1991 |
| EP | 0 554 818 A2 | 8/1993 |
| EP | 0 664 113 A2 | 7/1995 |
| EP | 0 784 970 A2 | 7/1997 |
| EP | 0 823 252 A2 | 2/1998 |
| EP | 0 911 345 A2 | 4/1999 |
| EP | 1 166 767 A2 | 1/2002 |
| GB | 2 331 302 | 5/1999 |
| GB | 2 380 938 | 4/2003 |
| JP | 10067630 | 3/1998 |
| JP | 2004339108 A | 12/2004 |
| WO | WO 95/04082 | 2/1995 |
| WO | WO 96/00461 | 1/1996 |
| WO | WO 98/09608 | 3/1998 |
| WO | WO 99/15135 | 4/1999 |

OTHER PUBLICATIONS

National Starch Personal Care Sunscreen Formulation, "Facial Clear Sunscreen Gel SPF 30—Water Resistant 11716-6-7", published Mar. 31, 2004, www.personalcarepolymers.com.
Modified Starches: Properties and Uses, Würzburg, Ed., CRC Press, Inc., Florida (1986).
Starch: Chemistry & Technology, vol. III—Industrial Aspects, Ch. XXII, "Production & Use of Pregelatinized Starch," R.L. Whistler et al., Ed., Academic Press, NY (1967).
Questel English Abstract of JP8193055A.
Fitzpatrick, J., "Xanthan Gum—The Natural Water for Cosmetic and Personal Care Products", In-Cosmetics, Mar. 1993, London UK vol. 2, pp. 37-40.

(Continued)

*Primary Examiner* — Mina Haghighatian
*Assistant Examiner* — Luke Karpinski
(74) *Attorney, Agent, or Firm* — Norris McLaughlin & Marcus, P.A.

(57) ABSTRACT

Sunscreen compositions comprising one or more sunscreen agents (inorganic and combinations of inorganic and organic), one or more film forming polymers (synthetic or naturally derived), and heat treated xanthan gum. The sunscreen composition provides higher pre- and post-immersion SPF values, as well as a means for reducing the amount of sunscreen agents in a formulation without forfeiting efficacy.

22 Claims, No Drawings

(56) References Cited

OTHER PUBLICATIONS

Vanzan Xanthan Gum, Vanderbilt Report No. 916.
Derwent Abstract of French Patent No. 2 606 423.
Patent Abstracts of Japan of Japanese Patent No. 11-236310.
Derwent Abstract No. 0007832191 of Japanese Patent No. 08-231354.
Derwent Abstract No. 0007114991 of Japanese Patent No. 07-69838.
Derwent Abstract No. 0006501880 of Japanese Patent No. 05-221838.
Derwent Abstract No. 0008415177 of Japanese Patent No. 09-255534.
Derwent Abstract No. 0004242616 of Japanese Patent No. 62-263111.
Derwent Abstract No. 0010037278 of Japanese Patent No. 2000-053552.
JP Abstract of Japanese Patent No. 07-061910.
JP Abstract of Japanese Patent No. 63-150215.
Torres et al, Bioprocess Engineering 12 (1995) 41-46, p. 46.
European Search Report for corresponding European Application No. EP 08001522.5 dated May 15, 2015.
Chinese Office Action for corresponding Chinese Application No. 2008-019104 dated Apr. 30, 2013.

* cited by examiner

SUNSCREEN COMPOSITIONS

BACKGROUND OF THE INVENTION

1. Technical Field

The present invention is directed towards skincare compositions. More particularly, the present invention is directed towards sunscreen compositions having improved efficacy in protection from ultraviolet radiation.

2. Background Information

Consumers are increasingly concerned about the effects of ultraviolet ('UV') radiation on the skin, and with good reason. Skin cancer has become one of the leading forms of cancer, annually affecting millions globally. Demand for UV protection has made the sun care market one of the fastest growing personal care sectors.

Commercially viable sun care products should provide a variety of benefits, such as high Sun Protection Factor (SPF) values, protection from UV-A and UV-B radiation (also known as broad-spectrum protection), water resistance and rub-off resistance, aesthetically pleasing products, and convenient application.

When formulating these products, consumer use should be considered. For example, swimming or mild perspiration is often sufficient to remove most commercially available sunscreen formulations from a person's skin, necessitating multiple applications. Such repeated applications are inconvenient, costly and typically results in the consumer delaying reapplication of the sunscreen, which may lead to sunburn.

Accordingly, higher SPF values, broad spectrum protection, enhanced water and rub-off resistance, the need for aesthetically pleasing products, and convenience have become increasingly important in sun protection formulations. Further, formulators continue to search for ways to not only increase the SPF value of formulations, but also to increase the efficacy of a sunscreen without increasing the actual level of the sunscreen actives within the formulation.

Additionally, formulators are left with little choice in the type of rheology modifiers used in formulations, particularly those containing actives (or agents) such as inorganic particulate sunscreen agents. Historically, xanthan gum has been the thickener of choice; however, this thickener contributes no benefit with respect to SPF enhancement.

Film forming polymers are used widely in personal care products for functions such as hair fixatives, SPF retention, water resistance, rub-off resistance, fragrance retention, and so forth and are well known in the art. These polymers can be both synthetic and naturally derived. The polymers are typically used in a variety of applications, including sun protection, to enhance the water and rub-off resistance of the UV filters. With the advent of higher SPF products, the challenge has been to create these sun protection formulations without increasing either the use level of the polymer or UV filters or both. Doing so causes unpleasant aesthetics and increased cost.

Therefore, there is a need for a sunscreen formulation that provides both water resistance and higher SPE values when applied to a person, both before and after immersion in water, in particular, one that provides these benefits without the need to increase the amount of sunscreen active or agent.

SUMMARY OF THE INVENTION

According to the present invention, a synergy has been discovered between heat-treated xanthan gum (e.g., xanthan gum having an INCI designation 'dehydroxanthan gum') and film forming polymers that results in SPF enhancement. This enhancement allows for higher SPF values both before and after water immersion. This synergy also allows for the reduction of amount of sunscreen agents used in a formulation without sacrificing SPF efficacy. Thus, this synergistic combination of UV filter, polymer, and heat treated xanthan gum results in a very useful tool to create higher SPF sun protection and cosmetic formulations.

"Synergistic" for the purpose of the present invention refers to the action of two or more substances achieving an effect greater than that possible with any of the individual components (i.e., the sum being greater than the parts).

"Heat treated" for the purpose of the present invention refers to xanthan gum that is heated for a given temperature and time. An example would be xanthan gum that is heated at 60° C. for at least 30 minutes to moisture content of less than about 8%.

Accordingly, the present invention provides in one aspect a sunscreen composition that is formulated with at least one or more sunscreen actives, with one or more of sunscreen actives being at least one inorganic sunscreen active. The composition further includes one or more film forming polymers and heat treated xanthan gum. With the one or more film forming polymers and heat treated xanthan gum, sunscreen compositions in one aspect provide a higher SPF value in such compositions than sunscreen compositions wherein the heat treated xanthan gum is replaced with non-heat treated xanthan gum.

In one aspect, sunscreen compositions according to the present invention include one or more sunscreen actives present in an amount of about 0.25 to about 30% by weight, based on total weight of the composition. In a further aspect, the one or more sunscreen actives include one or more particulate sunscreen actives. In even another aspect, the one or more particulate sunscreen actives is at least an inorganic sunscreen active such as zinc oxide and/or titanium dioxide. In one aspect, sunscreen compositions according to the present invention include at least one or more inorganic sunscreen actives in a water phase of the composition.

In one embodiment, sunscreen composition according to the present invention include one or more sunscreen actives wherein at least one of the actives is at least one or more particulates chosen from, for example, clays, agars, guars, nanoparticles, native and modified starches, modified cellulosics, zinc oxide, titanium dioxide and combinations thereof. In another embodiment, sunscreen compositions according to the present invention include one or more modified starches such as octenyl succinate (OSA) modified starch, modified corn starch and combinations thereof. In even another embodiment, sunscreen compositions according to the present invention include one or more sunscreen actives wherein at least one of the actives is an organic sunscreen active. In another aspect, sunscreen composition according to the present invention include one or more organic sunscreen actives chosen from, for example, ethylhexyl methoxycinnamate (octinoxate), ethylhexyl salicylate (octisalate), butylmethoxydibenzoylmethane, methoxydibenzoylmethane, avobenzone, benzophenone-3 (oxybenzone), octocrylene, aminobenzoic acid, cinoxate, dioxybenzone, homosalate, menthyl anthranilate, octocrylene, octisalate, oxybenzone, padimate O, phenylbenzimidazole sulfonic acid, sulisobenzone, trolamine salicylate and combinations thereof.

In one aspect, sunscreen compositions according to the present invention include one or more film forming polymers present in an amount of about 0.05 to about 10% by weight, based on total weight of the composition. In another aspect, sunscreen compositions according to the present invention include one or more film forming polymers wherein at least one of the polymers is an acrylates copolymer. In even another aspect, sunscreen compositions according to the present invention include one or more film forming polymers wherein at least one of the polymers is a polyurethane copolymer.

In one aspect, sunscreen compositions according to the present invention include heat treated xanthan gum present in an amount of about 0.05 to about 20% by weight, based on total weight of the composition.

In one embodiment, sunscreen compositions according to the present invention are in the form of an oil-in-water emulsion.

Sunscreen compositions according to the present invention can further optionally include one or more active agents. Non-limiting examples of such actives include anti-acne agents, antimicrobial agents, anti-inflammatory agents, analgesics, anti-erythemal agents, antiruritic agents, antiedermal agents, antipsoriatic agents, antifungal agents, skin protectants, vitamins, antioxidants, scavengers, antiirritants, antibacterial agents, antiviral agents, antiaging agents, protoprotection agents, hair growth enhancers, hair growth inhibitors, hair removal agents, antidandruff agents, anti-seborrheic agents, exfoliating agents, wound healing agents, anti-ectoparacitic agents, sebum modulators, immunomodulators, hormones, botanicals, moisturizers, astringents, cleansers, sensates, antibiotics, anesthetics, steroids, tissue healing substances, tissue regenerating substances, amino acids, peptides, minerals, ceramides, hydroxyalkyl urea, biohyaluronic acids, vitamins, skin lightening agents, self tanning agents, coenzyme Q10, niacinimide, capcasin, caffeine, and combinations thereof.

In addition to the active agents, sunscreen compositions according to the present invention can optionally include one or more adjuvants. Sunscreen compositions according to the present invention can also optionally include one or more conditioning agents. Likewise, sunscreen compositions according to the present invention can optionally include one or more preservatives. Sunscreen compositions according to the present invention can further optionally include one or more aesthetic enhancers. Non-limiting examples of such aesthetic enhancers include corn starch, tapioca starch and combinations thereof. It will be recognized by one skilled in the art that any combination of these optional ingredients may be utilized in the present sunscreen compositions.

In even a further embodiment, the present invention includes a method of reducing UV radiation on a substrate by applying to the substrate an effective amount of a sunscreen composition formulated with at least one or more sunscreen actives, with one or more of sunscreen actives being at least one inorganic sunscreen active. The composition further includes one or more film forming polymers and heat treated xanthan gum.

DETAILED DESCRIPTION

The present invention is directed to a composition comprising one or more sunscreen actives or agents (including particulate and combinations of particulate and organic), one or more water dispersible film forming polymers (synthetic or naturally derived), and heat treated xanthan gum. These compositions are suitable in a variety of applications, including those found in cosmetic and personal care.

The hydrocolloid xanthan gum is a polysaccharide gum derived from the bacterium *Xanthomonas* and is well known in the art. It has pseudo-plastic or shear-thinning behavior characterized by a decrease in apparent viscosity in response to an increase in shear rate.

Xanthan gum is typically used as a rheology modifier in a variety of industrial applications, functioning in thickening, viscosifying and gelling. It has also been used to impart stability to emulsions and for its suspending properties to prevent the settling out of solids. Xanthan gum's limited ability to be dispersed in either hot or cold water restricts its use in a broad variety of applications, including pharmaceuticals, household products, foods, and personal care products.

Heat treated xanthan gums according to the present invention differ from other xanthan gum in that they increase solution viscosity (at 1% solids in an aqueous solution) at least about 10,000 cps compared to the solution viscosity (at 1% solids in an aqueous solution) of xanthan gum prior to heat treatment. In another aspect, xanthan gums according to the present invention provide an increase in solution viscosity of up to at least about 12,500 cps over the viscosity of xanthan gum prior to treatment. In even another aspect, xanthan gums according to the present invention increase solution viscosity up to at least about 15,000 cps over the viscosity of xanthan gum prior to treatment, depending upon the heat treatment conditions used.

Heat treated xanthan gum typically has improved dispersibility over non-heat treated gum, such that under given conditions of temperature and agitation, the time to fully disperse the heat treated gum is typically reduced by 25% versus gums that are not heat treated. In another aspect, the time to fully disperse is reduced by 50%. In even another aspect, the time for the gum to disperse is reduced by 70% compared to non-heat treated xanthan. The heat treated gum also generally provides improved thickening ability, rheology modification, emulsion stabilization, suspending ability, texture enhancement, film forming and foam stabilization.

Heat treated xanthan gum provides clear to translucent clarity and is easy to use as it is dispersible in either hot or cold water and needs no neutralization. It exhibits tolerance to salt and extreme pH, particularly in the range of about 2 to about 12, is biodegradable, and may be labeled as natural.

Heat modification of xanthan gum improves the ease of use, including ease of dispersing in solution with fewer tendencies to form fish eyes. Heat modification also not only improves thickening efficiency, but also aesthetics such as gel texture, (e.g., reducing the stringiness or pituitousness of the long texture). In addition, the viscosity enhancing effect of heat treated xanthan can occur in a variety of pH and salt ranges. Heat treated xanthan gum is compatible with anionic, cationic or nonionic polymers, allowing it to be formulated with a variety of commonly used additives.

Xanthan gum that has been further processed by heat treatment is known in the art. For example, European Publication No. 0 321 216 A describes enhancing the viscosity profile of xanthan gum by thermally treating it. Heat treatment of xanthan gum is also described in Japanese Application No. 8-193055, which heat treats xanthan gum in its powdered form. U.S. Publication No. 2003-0108505 A1 describes the use of heat treated xanthan gum in hair cosmetics.

Any xanthan gum may be used as a starting material for heat treatment. Such xanthan gums are commercially available, for example, from Archer Daniels Midland and CP Kelco. These gums typically have a moisture content of from 8 to about 14 weight %, based on total weight of the gum, with about 10-11 weight % being the average amount of moisture.

Heat treatment can be performed on xanthan gum to reduce its moisture content to less than about 8%. In another aspect, the gum can be heat treated so as to reduce its moisture content to less than about 5%. In even another aspect, xanthan gum can be heat treated so as to reduce its moisture content to less than about 1%, or substantially anhydrous. Heat treatment can occur at a temperature of at least about 60° C. The gum can be heat treated, for example, for a period of time of about 30 minutes to at least 2 hours, depending upon the level of moisture in the gum that is sought and the temperature at which the gum is heat treated.

Temperature and time of heat treatment can be adjusted by one skilled in the art in order to achieve the desired viscosity, dispersibility, gel texture, solution clarity, and any other properties desired. These properties are also dependent upon the xanthan gum starting material used (e.g., its grade, viscosity, molecular weight, and particle size).

Heat treatment of xanthan gum can be accomplished by any of a variety of methods known in the art, including, without limitation, the use of ovens, fluidized beds, infrared and microwave heat treatments. The particle size of the resultant heat-treated xanthan gum can be adjusted using methods known in the art such as milling, or the particle size can be adjusted prior to heat treatment.

Heat treated xanthan gum according to the present invention can optionally be further modified either before or after heat treatment. For example, the gum can be chemically, enzymatically or physically modified. Such processes are known in the art. Suitable chemical modifications include, for example, gum conversion by oxidation, enzyme conversion, acid hydrolysis, heat and/or acid dextrinization, or shear. Suitable chemical derivatives include esters, such as acetate, and half esters, such as succinate, octenyl succinate and tetradecenyl succinate; phosphate derivatives; ethers such as hydroxyalkyl ethers and cationic ethers; or any other derivatives or combinations thereof. Modification can also be by chemical crosslinking. Crosslinking agents suitable for use herein include phosphorus oxychloride, epichlorohydrin, sodium trimetaphosphate and adipic-acetic mixed acid anhydrides. Suitable enzymatic treatments that produce additional derivatives are also included. Suitable processes for physical modification include, for example, agglomeration, spray drying, drum drying, chilsonation, jet cooking and extrusion.

Heat treated xanthan gum according to the present invention can be purified by any method known in the art to remove off flavors, colors, and contaminants that are native to the gum or are created during the modifications and/or heat treatment processes as long as the heat treatment is not substantially impacted.

Heat treated xanthan gum may be used in a variety of compositions, including without limitation, cosmetic and personal care compositions, detergents and household cleaning compositions, paper products, oil field chemicals, and food and beverage compositions. Cosmetic and personal care compositions include skin lotions and creams, skin gels, serums and liquids, facial and body cleansing products, wipes, liquid and bar soap, color cosmetic formulations, make-ups, foundations, sun care products, sunscreens, sunless tanning formulations, shampoos, conditioners, hair color formulations, hair relaxers, products with AHA and BHA and hair fixatives such as sprays, gels, mousses, pomades, and waxes, including low VOC hair fixatives and sunscreens. The compositions may be in any form, including without limitation, emulsions, gels, liquids, sprays, solids, mousses, powders, wipes, or sticks.

Heat treated xanthan gum may be formulated into compositions at any level which provides the desired properties. Typically, a lesser amount of heat-treated xanthan gum will be required to achieve the same properties and functionality as native or non-heat treated xanthan gum. Heat treated xanthan gums can be used in compositions in an amount of at least about 0.05 to about 20% by weight, based on total weight of the composition. In another aspect, the heat treated gum is present in the composition in an amount of about 0.05% to about 5% by weight, based on total weight of the composition. The amount used will depend not only upon the properties desired, but also upon the degree of heat treatment of the gum, as well as other ingredients in the composition.

Heat treated xanthan gum can be incorporated into the composition in the same manner as native xanthan gum. For example, heat-treated xanthan gum can be dispersed in water and then the remaining components added.

In addition to the heat treated xanthan gum, compositions according to the present invention further include polymers and copolymers capable of forming a film. Useful film forming polymers can either be synthetic or naturally derived. For example, film forming polymers according to the present invention include water dispersible polymers, either naturally or synthetically derived, that, when added to water at about 5% solids at about 22° C. and at a pH of about 5.5, do not give a clear solution. Like xanthan gums, film forming polymers can be used in a variety of compositions, for example, cosmetic and personal care compositions, detergents and household cleaning compositions, paper products, oil field chemicals, and food and beverage compositions. Cosmetic and personal care compositions include, for example, skin lotions and creams, skin gels, serums and liquids, facial and body cleansing products, wipes, liquid and bar soap, color cosmetic formulations, make-ups, foundations, sun care products, sunscreens, sunless tanning formulations, shampoos, conditioners, hair color formulations, hair relaxers, products with AHA and BHA and hair fixatives such as sprays, gels, mousses, pomades, and waxes, including low VOC hair fixatives and sunscreens. These cosmetic and personal care compositions may be in any form, including with out limitation, emulsions, gels, liquids, sprays, solids, mousses, powders, wipes, or sticks.

Non-limiting examples of synthetic, water dispersible film forming polymers suitable for use in the present invention include: from National Starch and Chemical Company, AMPHOMER and AMPHOMER LV-71 polymers (octylacrylamide/acrylates/butylaminoethyl methacrylate copolymer), AMPHOMER HC polymer (acrylates/octylacrylamide copolymer) BALANCE 0/55 and BALANCE CR polymers (acrylates copolymer), BALANCE 47 polymer (octylacrylamide/acrylates/butylaminoethyl methacrylate copolymer), RESYN 28-2930 polymer (VA/crotonate/vinyl neodecanoate copolymer), RESYN 28-1310 polymer (VA/Crotonate copolymer), DynamX polymer (polyurethane-14 (and) AMP-Acrylates copolymer), RESYN XP polymer (acrylates/octylacrylamide copolymer), STRUCTURE 2001 (acrylates/steareth-20 itaconate copolymer) STRUCTURE 3001 (acrylates/ceteth-20 itaconate copolymer), YODOSOL 32A707, YODOSOL GH15, YODOSOL GH32, YODOSOL GH33, YODOSOL GH34, YODOSOL GH35, YODOSOL GH256, YODOSOL GH800, YODOSOL GH810, YODOSOLGH32A707F, YODOSOL GH15F, YODOSOL GH34F, YODOSOL GH800F, YODOSOL GH810F, YODOSOL GH800PF (acrylates copolymer), YODOSOL GH52, YODOSOL GH52-OP (styrene/methacrylamide/acrylates copolymer), YODOSOL GH265 (polyacrylate-2), YODOSOL GH840, YODOSOL GH41F, YODOSOL GH4I (styrene/acrylates copolymer), YODOSOL PUD (polyurethane-10 (and) PEG-12 dimethicone (and) alcohol), DERMACYL AQF (acrylates copolymer), DERMACRYL C (proposed: acrylates copolymer) and DERMACRYL 79 and LT polymers (acylates/octyacrylamide copolymer); from ISP, OMNIREZ-2000 (PVM/MA half ethyl ester copolymer), GANTREZ A-425 (butyl ester of PVM/MA copolymer), GANTREZ AN-119 PVM/MA copolymer, GANTREZ ES 225 (ethyl ester of PVM/MA copolymer), GANTREZ ES-425 (butyl ester of PVM/MA copolymer), AQUAFLEX XL-30 (Polyimide-1), ALLIANZ LT-120 (Acrylates/C1-2 Succinates/Hydroxyacrylates Copolymer), ALLIANZ OPT (Acrylates/$C_{12-22}$ Alkyl Methacrylate Copolymer), STYLEZE CC-10 (PVP/DMAPA Acrylates Copolymer), STYLEZE 2000 (VP/Acrylates/Lauryl Methacrylate Copolymer), STYLEZE W-20 (Polyquaternium-55), ADVANTAGE PLUS (VA/Butyl Maleate/Isobornyl Acrylate Copolymer); from BASF, ULTRAHOLD STRONG (acrylic acid/ethyl acrylate/t-butyl acrylamide), LUVIMER 100 P (t-butyl acrylate/ethyl acrylate/methacrylic acid), LUVIMER 36D (ethyl acrylate/t-butyl acrylate/methacrylic acid), LUVISET PUR (Polyurethane-1), LUVISET Clear (VP/Methacrylamide/Vinyl Imidazole Copolymer), LUVIFLEX SOFT (Acrylates Copolymer), ULTRAHOLD 8 (Acrylates/Acrylamide Copolymer), LUVIFLEX Silk (PEG/PPG-25/25 Dimethicone/Acrylates Copolymer), LUVISET CAN (VA/crotonate/vinyl neodecanoate copolymer), LUVIMER PRO55 (acrylates copolymer); from Amerchol, AMERHOLD DR-25 (acrylic acid/methacrylic acid/acrylates/methacrylates); from Rohm and Haas, ACUDYNE 258 (acrylic acid/methacrylic acid/acrylates/methacrylates/hydroxy ester acrylates), ACUDYNE DHR (acrylates/hydroxyesters acrylates copolymer) ALLIANZ OPT (Acrylates/C12-22 Alkyl Methacrylate Copolymer); from Mitsubishi and distributed by Clariant, DIAFORMER Z-301, DIAFORMER Z-SM, and DIAFORMER Z-400 (methacryloyl ethyl betaine/acrylates copolymer), ACUDYNE 180 (Acrylates/Hydroxyesters Acrylates Copolymer), ACUDYNE SCP (Ethylenecarboxyamide/AMPSA/Methacrylates Copolymer), and the ACCULYN rheological modifiers; from ONDEO Nalco, FIXOMER 40 (acrylates copolymer), FIXOMER A-30 and FIXOMER N-28 (INCI names: methacrylic acid/sodium acrylamidomethyl propane sulfonate copolymer); from Eastman Chemical, Eastman polymer AQ38S and AQ55S (diglycol/CHEM/isophthalates/SIP copolymer); from Interpolymer, SYNTRAN 5009 AND SYNTRAN 5760 (Styrene/Acrylates/Ammonium Methacrylate Copolymer), SYNTRAN 5190 (acrylates copolymer), SYNTRAN 5900 and 5902 (polystyrene), SYNTRAN 5903, 5904, 5905 (styrene/acrylates copolymer), SYNTRAN KL-219C (ammonium acrylates copolymer), SYNTRAN PC 5112 (polyacrylate-16), SYNTRAN PC5208 (polyacrylate-15), SYNTRAN PC5100 (Polyacrylate-21 and Acrylates/Dimethylaminoethyl Methacrylate Copolymer) SYNTRAN PC5107 and PC5117 (Polyacrylate-18 and Polyacrylate-19), SYNTRAN PC5205 and PC5227 (Polyacrylate-15 and Polyacrylate-17); from Noveon, FIXATE G-100 (AMP-Acrylates/Allyl Methacrylate Copolymer), FIXATE PLUS (Polyacrylates-X), CARBOPOL Ultrez 10 (Carbomer), CARBOPOL Ultrez 20 (Acrylates/C10-30 Alkyl Acrylates Copolymer), AVALURE AC series (Acrylates Copolymer), AVALURE UR series (Polyurethane-2, Polyurethane-4, PPG-17/IPDI/DMPA Copolymer); from Inolex Chemical Company, LEXOREZ TL8 (Trimethylpentanediol/Adipic Acid Copolymer, LEXOREZ TC8 and LEXOREZ TC-1 (INCI names: Trimethylpentanediol/Adipic Acid/Isononanoic Acid Copolymer), LEXOREZ 200 (Trimethylpentanediol/Adipic Acid/Glycerin Crosspolymer), LEXOREZ 100 (Adipic Acid/Diethylene Glycol/Glycerin Crosspolymer), LEXFILM SUN (polyester-7 (and) neopentyl glycol diheptanoate), LEXFILM SPRAY (polyester-10 (and) propylene glycol dibenzoate); from Dow Corning: DOW CORNING FA 4002 ID SILICONE ACRYLATE (Isododecane (and) Acrylates/Polytrimethylsiloxymethacrylate Crosspolymer), DOW CORNING FA4001 ID SILICONE ACRYLATE (Cyclopentasiloxane (and) Acrylates/Polytrimethylsiloxymethacrylate Copolymer); and any combination of the foregoing. (For the purpose of the present invention, it is understood that the film forming polymers may be used in their water dispersible or water soluble state. For example, at least some of the above mentioned commercial film formers are not render water soluble with some degree of neutralization; otherwise they may be soluble only in organic solvent.)

Useful film forming polymers can further optionally include combinations of other water dispersible synthetic polymers as well as ones naturally derived, either alone or in combination. Natural film forming water dispersible polymers suitable for use in the present invention include any polysaccharide derivative (both native and modified). For example, native starch as used herein refers to starch as it is found in nature. Also suitable are starches derived from a plant obtained by standard breeding techniques, including crossbreeding, translocation, inversion, transformation or any other method of gene or chromosome engineering to include variations thereof. In addition, starch derived from a plant grown from artificial mutations and variations of the above generic composition that may be produced by known standard methods of mutation breeding are also suitable herein.

Typical sources for the starches are cereals, tubers, roots, legumes and fruits. The native source can be corn, pea, potato, sweet potato, banana, barley, wheat, rice, sago, amaranth, tapioca, arrowroot, canna, sorghum, and waxy or high amylose varieties thereof. The term "waxy" is intended to refer to those starches containing at least about 95 percent by weight amylopectin (the remainder being amylose), and the term "high amylose" is intended to refer to those starches containing at least about 40 percent by weight amylose (the remainder being amylopectin). In another aspect, high amylose starch refers to those starches containing at least about 70 percent by weight amylose.

Modifications to native starches suitable for the present invention can be performed using any modification known in the art, including physical, chemical and/or enzymatic modifications, to obtain the desired film forming attributes.

Physically modified starches suitable for use herein include sheared starches, thermally-inhibited starches described in the family of patents represented by International Publication No. WO 95/04082, and resistant starches described in the family of patents represented by U.S. Pat. No. 5,593,503.

Chemically modified starches include, without limitation, those which have been crosslinked, acetylated and organically esterified, hydroxyethylated and hydroxypropylated, phosphorylated and inorganically esterified, cationic, anionic, nonionic, amphoteric and zwitterionic, and succinate and substituted succinate derivatives thereof. Such modifications are known in the art, for example, in the text MODIFIED STARCHES: PROPERTIES AND USES, Würzburg, Ed., CRC Press, Inc., Florida (1986).

Conversion products derived from any of the starches, including fluidity or thin-boiling starches prepared by oxidation, enzyme conversion, acid hydrolysis, heat and or acid dextrinization, thermal and or sheared products may also be useful herein.

Further suitable are pregelatinized starches known in the art and disclosed, for example, in U.S. Pat. Nos. 4,465,702, 5,037,929, 5,131,953 and 5,149,799. Conventional procedures for pregelatinizing starch are also known to those skilled in the art and described, for example, in STARCH: CHEMISTRY AND TECHNOLOGY, VOL. III—INDUSTRIAL ASPECTS, Chpt.

XXI—"Production and Use of Pregelatinized Starch", R. L. Whistler and E. F. Paschall, Ed., Academic Press, New York (1967).

Any starch or starch blend having suitable properties for use herein may be purified by any method known in the art to remove starch off colors that are native to the polysaccharide or created during processing. Suitable purification processes for treating starches are disclosed, for example, in the family of patents represented by European Patent Publication No. 0 554 818 A2. Alkali washing techniques, for starches intended for use in either granular or pregelatinized form, are also useful and described in the family of patents represented by U.S. Pat. Nos. 4,477,480 and 5,187,272.

Additional suitable starches are starches capable of emulsifying or encapsulating an active ingredient so that there is no need for additional encapsulating or emulsifying agents. Such starches include, without limitation, hydroxyalkylated starches such as hydroxypropylated or hydroxyethylated starches, and succinylated starches such as octenyl succinylated or dodecyl succinylated starches. In one embodiment, emulsifying or encapsulating starches are used so that a solution or dispersion of the film material (starch component, active agent, and optional additives) may be stored for later processing. The hydroxyalkylated starches have the added advantage of forming a softer film so that there is less or no need for a plasticizer.

Other modified polysaccharides can be used in addition to starch, such as cellulose, chitin, glucosaminoglyeans, proteoglycans, chitosan, heparin, chondroitin, glycogen and any combination of the foregoing.

The naturally derived water dispersible film forming component can be a single modified or native starch, single modified cellulosic, a blend of modified starches, blend of native starches, blend of modified cellulosics, or a blend of both modified starches and cellulosics and native starches. Blends may be useful for lowering the cost of the film or for more easily achieving a variety of desirable properties and functionalities.

Examples of commercial starches together with their INCI names that may be used in the present invention as film formers include the following: from National Starch and Chemical Company, AMAZE® polymer (corn starch modified), CELQUAT® LS-50 resin (polyquaternium-4/hydroxypropyl starch copolymer), STRUCTURE® XL polymer (hydroxypropyl starch phosphate); from the Croda Company, CROSTYLE MFP (trimethyl quaternized maize starch); and from ONDEO Nalco, SENSOMER C1-50 (starch hydroxypropyl trimonium chloride) and any combination of the foregoing.

A non-limiting example of a commercial cellulosic together with its INCI name that may be used in the present invention as film formers include from National Starch and Chemical Company, CELQUAT® LS-50 resin (polyquaternium-4/hydroxypropyl starch copolymer) and any combination of the foregoing.

The film forming component of the invention also comprises blends of both synthetic and naturally derived water dispersible polymers.

Suitable sunscreen agents or actives useful in the present invention include any particulate sunscreen active that absorbs, scatters, or blocks ultraviolet (UV) radiation, such as UV-A and UV-B. Non-limiting examples of suitable particulate sunscreen agents include clays, agars, guars, nanoparticles, native and modified starches, modified cellulosics, zinc oxide, and titanium dioxide and any combination of the foregoing. Modified starches include, for example, DRY-FLO® PC lubricant (aluminum starch octenylsuccinate), DRY-FLO® AF lubricant (corn starch modified), DRY-FLO® ELITE LL lubricant (aluminum starch octenylsuccinate (and) lauryl lysine), DRY-FLO® ELITE BN lubricant (aluminum starch octenylsuccinate (and) boron nitride), all commercially available from National Starch and Chemical Company.

In one aspect, the sunscreen agents include those that form a physical and/or chemical barrier between the UV radiation and the surface to which they are applied. Non-limiting examples of suitable sunscreen agents include ethylhexyl methoxycinnamate (octinoxate), ethylhexyl salicylate (octisalate), butylmethoxydibenzoylmethane, methoxydibenzoylmethane, avobenzone, benzophenone-3 (oxybenzone), octocrylene, aminobenzoic acid, cinoxate, dioxybenzone, homosalate, methyl anthranilate, octocrylene, octisalate, oxybenzone, padimate O, phenylbenzimidazole sulfonic acid, sulisobenzone, trolamine salicylate and any combination of any of the foregoing The sunscreen agents can be used in a variety of compositions, including without limitation, cosmetic and personal care compositions, detergents and household cleaning compositions, paper products, oil field chemicals, and food and beverage compositions. Cosmetic and personal care compositions include skin lotions and creams, skin gels, serums and liquids, facial and body cleansing products, wipes, liquid and bar soap, color cosmetic formulations, make-ups, foundations, sun care products, sunscreens, sunless tanning formulations, shampoos, conditioners, hair color formulations, hair relaxers, products with AHA and BHA and hair fixatives such as sprays, gels, mousses, pomades, and waxes, including low VOC hair fixatives and sunscreens. The compositions can be in any form, including without limitation, emulsions, gels, liquids, sprays, solids, mousses, powders, wipes, or sticks.

Generally, sunscreen compositions or formulations contain about 0.25 to about 30% by weight, based on total weight of the composition, of one or more sunscreen agents/actives or UV filters.

Sunscreen compositions according to the present invention can optionally further include active agents. Suitable active agents include, for example, anti-acne agents, antimicrobial agents, anti-inflammatory agents, analgesics, anti-erythemal agents, antiruritic agents, antiedermal agents, antipsoriatic agents, antifungal agents, skin protectants, vitamins, antioxidants, scavengers, antiirritants, antibacterial agents, antiviral agents, antiaging agents, protoprotection agents, hair growth enhancers, hair growth inhibitors, hair removal agents, anti-dandruff agents, anti-seborrheic agents, exfoliating agents, wound healing agents, anti-ectoparacitic agents, sebum modulators, immunomodulators, hormones, botanicals, moisturizers, astringents, cleansers, sensates, antibiotics, anesthetics, steroids, tissue healing substances, tissue regenerating substances, hydroxyalkyl urea, amino acids, peptides, minerals, ceramides, biohyaluronic acids, vitamins, skin lightening agents, self tanning agents, coenzyme Q10, niacinimide, capcasin, caffeine, and any combination of any of the foregoing.

Sunscreen compositions according to the present invention can optionally include one or more aesthetic enhancers (i.e., a material that imparts desirable tactile, visual, taste and/or olfactory properties to the surface to which the composition is applied) and can be either hydrophilic or hydrophobic. Non-limiting examples of commercial aesthetic enhancers together with their INCI names that may be used in the present invention include from National Starch and Chemical Company, PURITY® 21C starch (zea maize (corn) starch) and TAPIOCA PURE (tapioca starch), as well as combinations thereof.

Sunscreen compositions according to the present invention can optionally include one or more adjuvants, such as pH adjusters, emollients, humectants, conditioning agents, moisturizers, chelating agents, propellants, rheology modifiers and emulsifiers such as gelling agents, colorants, fragrances, odor masking agents, UV stabilizer, preservatives, and any combination of any of the foregoing. Examples of pH adjusters include, but are not limited to, aminomethyl propanol, aminomethylpropane diol, triethanolamine, triethylamine, citric acid, sodium hydroxide, acetic acid, potassium hydroxide, lactic acid, and any combination thereof.

Suitable conditioning agents include, but are not limited to, cyclomethicone; petrolatum; dimethicone; dimethiconol; silicone, such as cyclopentasiloxane and diisostearoyl trimethylolpropane siloxy silicate; sodium hyaluronate; isopropyl palmitate; soybean oil; linoleic acid; PPG-12/saturated methylene diphenyldiisocyanate copolymer; urea; amodimethicone; trideceth-12; cekimonium chloride; diphenyl dimethicone; propylene glycol; glycerin; hydroxyalkyl urea; tocopherol; quaternary amines; and any combination thereof.

Suitable preservatives include, but are not limited to, chlorophenesin, sorbic acid, disodium ethylenedinitrilotetraacetate, phenoxyethanol, methylparaben, ethylparaben, propylparaben, phytic acid, imidazolidinyl urea, sodium dehydroacetate, benzyl alcohol, methylehloroisothiazolinone, methylisothiazolinone, and any combination thereof. The sunscreen composition generally contains from about 0.001% to about 20% by weight of preservatives, based on 100% weight of total sunscreen composition. In another aspect, the composition contains from about 0.1% to about 10% by weight of preservatives, based on 100% weight of total sunscreen composition.

In one aspect sunscreen compositions according to the present invention include a water phase. These sunscreen compositions can also optionally include any cosmetically acceptable solvent. Non-limiting examples of such solvents can include hydrocarbons, alcohols, esters and blends thereof.

Generally, sunscreen compositions according to the present invention contain at least one or more sunscreen actives or agents in an amount of about 0.25 to about 30% by weight, based on total weight of the compositions; one or more film forming polymers in an amount of about 0.05 to about 10% by weight, based on total weight of the composition; and heat treated xanthan gum in an amount of about 0.05 to about 20% by weight, based on total weight of the composition, with the remaining composition including other ingredients such as the above described adjuvants, active agents and aesthetic enhancers according to the desired end formulation. One skilled in the art would know which additional ingredients would be required. In another aspect, sunscreen compositions according to the present invention contain one or more film forming polymers in an amount of about 0.5 to about 5% by weight, based on total weight of the composition. In even another aspect, sunscreen compositions according to the present invention contain heat treated xanthan gum in an amount of about 0.05 to about 5% by weight, based on total weight of the composition.

The following examples are intended to exemplify the present invention but are not intended to limit the scope of the invention in any way. The breadth and scope of the invention are to be limited solely by the claims appended hereto.

EXAMPLES

The formulae described below contain at least two inorganic sunscreen agents—ZnO and $TiO_2$. Literature teaches that when formulating with both these types, they should not be in the same phase of the formulation, as agglomeration is likely to occur, resulting in a lower SPF value due to reduction of UV light scattering.

All formulations were prepared according to the follow procedure—

Xanthan gum is dispersed in water until completely hydrated. The remainder of Phase B less the UVB filter is combined and heated to 75° C., and the UVB filter added. Phase A ingredients are combined and heat to 75° C. Phase A is then added to Phase B and homogenized at 10,000 rpm for one minute. Cool to room temperature with stirring and add the Phase C ingredients, with the neutralizer added to adjust the pH to 7.

The results below demonstrate that the combination of both heat treated xanthan gum (Dehydroxanthan gum) and film-forming polymers (water-dispersible technologies, e.g., acrylates copolymer(s), polyurethanes, etc.) provides an unexpected boost in SPF. Through several experiments detailed here in the Examples, the scope of this unexpected boost is defined.

Example 1

Comparison of Sunscreen Formulations Containing Heat Treated Xanthan Gum versus Formulations wherein the Xanthan Gum is not Heat Treated Four sunscreen formulations were prepared as follows:

| Ingredient | Function | Formula 1[1] | Formula 2 | Formula 3 | Formula 4 |
|---|---|---|---|---|---|
| PHASE A | | | | | |
| Isohexadecane | Emollient | 1.5 | 1.5 | 1.5 | 1.5 |
| C12-C15 alkyl benzoate | Emollient | 3.0 | 3.0 | 3.0 | 3.0 |
| Cyclopentasiloxane | Emollient | 2.25 | 2.25 | 2.25 | 2.25 |
| Sorbitan Stearate | Emulsifier | 1.0 | 1.0 | 1.0 | 1.0 |
| Glyceryl Stearate (and) PEG-100 Stearate | Emulsifier | 2.0 | 2.0 | 2.0 | 2.0 |
| Octocrylene | UVB filter | 2.0 | 2.0 | 2.0 | 1.3 |
| Ethylhexyl Methoxycinnamate | UVB filter | 7.5 | 7.5 | 7.5 | 5.41 |
| Benzophenone-3 | UVB filter | 3.0 | 3.0 | 3.0 | 2.05 |
| ZnO (and) C12-C15 Alkyl Benzoate (and) Polyhydroxystearic Acid | UVA/B filter | 6.0 | 6.0 | 6.0 | 5.3 |
| PHASE B | | | | | |
| Water | | 54.25 | 54.25 | 58.65 | 60.64 |
| Dehydroxanthan Gum | Suspension agent, Rheology modifier | 0.5 | 0.0 | 0.5 | 0.5 |
| Xanthan Gum | Rheology modifier | 0.0 | 0.5 | 0.0 | 0.0 |
| Acrylates Copolymer | Film former | 4.4 | 4.4 | 0.0 | 4.4 |

-continued

| Ingredient | Function | Formula 1[1] | Formula 2 | Formula 3 | Formula 4 |
|---|---|---|---|---|---|
| Glycerin | Humectant | 3.0 | 3.0 | 3.0 | 3.0 |
| TiO$_2$ and Alumina and Silica and Sodium Polyacrylate | UVB filter | 7.0 | 7.0 | 7.0 | 5.05 |
| PHASE C | | | | | |
| Corn Starch Modified | Aesthetic enhancer | 2.0 | 2.0 | 2.0 | 2.0 |
| DMDM Hydantoin and Iodopropynyl Butylcarbamate | Preservative | 0.6 | 0.6 | 0.6 | 0.6 |
| Citric Acid (50%) | Neutralizer | qs to pH 7 | qs to pH 7 | qs to pH 7 | qs to pH 7 |
| TOTAL | | 100 | 100 | 100 | 100 |

[1]All values for each formula provided herein are in weight %, based on total weight of the composition or formulation.

The above formulations differ in that Formulation 1 was made with heat treated xanthan gum, Formulation 2 was made with non-heat treated xanthan gum, and Formulation 3 was made with heat treated xanthan gum but without the film forming polymer. Formula 4 is based on Formula 1 with the exception that the amount of all sunscreen actives (UV filters) has been reduced by 25% to determine whether a reduction in the amount of sunscreen agents will still provide an acceptable SPF value.

In-Vitro SPF Testing Procedure:

These formulations were submitted for in-vitro SPF testing to determine SPF values according to the following procedure—

All formulations were tested for SPF values under confidentiality by an outside testing laboratory (IMS Inc., Quarry Road Technology Park, 282 Quarry Road, Milford Conn., 06460-5508, USA). SPF values were obtained via their method entitled *IMS Inc In Vitro Sunscreen Waterproof/Water Resistance Protocol for Use with VITRO-SKIN® Substrate*. 2 µL/cm$^2$ of sample was applied to the VITRO-SKIN® substrate. The substrate was then agitated in a 40° C. water bath at 300 rpm for 80 minutes. SPF measurements were taken both before and after immersion at 10 different measurements sites using a Labsphere UV 1000S ultraviolet transmittance analyzer (Labsphere, Inc. North Sutton, N.H. 03260), with the resultant SPF value calculated as an average. These measurements are compared to a blank in each case (VITRO-SKIN® substrate with no test material applied).

Target SPF was 30. Test results provided below show a post-immersion value of 32.6 for Formulation 1 (heat treated xanthan gum formulation) versus 20.5 for Formulation 2 (non-heat treated xanthan gum formulation). Formulation 3 containing no acrylates copolymer was made to see if the combination of heat treated xanthan gum and acrylates copolymer was needed for a boost in SPF. The resulting SPF value (8.7) indicates that heat treated xanthan gum without the film former does not provide as effective water resistance in sunscreens as the combination of the two does. Combination with the film former also results in a higher pre-immersion or static SPF value, indicating that a better, more uniform film was formed when dried on the synthetic skin substrate.

TABLE 1

| | SPF Values | | | |
|---|---|---|---|---|
| In-vitro Data | Formulation 1 | Formulation 2 | Formulation 3 | Formulation 4 |
| Pre-immersion SPF | 47.9 | 49.8 | 33.9 | 40.9 |
| Post-immersion SPF | 32.6 | 20.5 | 8.7 | 35.6 (40 min) |
| | | | | 21.4 (80 min) |

Formula 4, which contains a 25% reduction in overall UV filter concentration versus Formula 1, shows a boost to still be quite evident, as 35.6 is close to the 32.6 from the original formulation (based on a 40-minute immersion (the time frame used in in-vivo studies to make a water resistance claim in sunscreens according to United States guidelines, as opposed to a very water resistant claim that is based on an 80-minute value).

Example 2

UV Filters

The following three formulations were prepared in order to study the effect of different sunscreen actives and their amount in providing UV protection—

| Ingredient | Function | Formula 5 | Formula 6 | Formula 7 |
|---|---|---|---|---|
| PHASE A | | | | |
| Isohexadecane | Emollient | 1.5 | 1.5 | 1.5 |
| C12-C15 alkyl benzoate | Emollient | 3.0 | 3.0 | 3.0 |
| Cyclopentasiloxane | Emollient | 2.25 | 2.25 | 2.25 |
| Sorbitan Stearate | Emulsifier | 1.0 | 1.0 | 1.0 |
| Glyceryl Stearate (and) PEG-100 Stearate | Emulsifier | 2.0 | 2.0 | 2.0 |
| Caprylic/Capric Triglyceride | Solubilizer | 0.0 | 6.25 | 6.25 |
| Isopropyl Myristate | Solubilizer | 0.0 | 6.25 | 6.25 |
| Octocrylene | UVB filter (org) | 2.0 | 0.0 | 0.0 |

-continued

| Ingredient | Function | Formula 5 | Formula 6 | Formula 7 |
|---|---|---|---|---|
| Ethylhexyl Methoxycinnamate | UVB filter (org) | 7.5 | 0.0 | 0.0 |
| Benzophenone-3 | UVB filter (org) | 3.0 | 0.0 | 0.0 |
| ZnO (and) C12-C15 Alkyl Benzoate (and) Polyhydroxystearic Acid | UVA/B filter (inorg) | 0.0 | 6.0 | 6.0 |
| PHASE B | | | | |
| Water | | 67.25 | 54.25 | 58.65 |
| Dehydroxanthan Gum | Suspension agent, Rheology modifier | 0.5 | 0.5 | 0.0 |
| Xanthan Gum | Rheology modifier | 0.0 | 0.0 | 0.5 |
| Acrylates Copolymer | Film former | 4.4 | 4.4 | 4.4 |
| Glycerin | Humectant | 3.0 | 3.0 | 3.0 |
| $TiO_2$ and Alumina and Silica and Sodium Polyacrylate | UVB filter (inorg) | 0.0 | 7.0 | 7.0 |
| PHASE C | | | | |
| Corn Starch Modified | Aesthetic enhancer | 2.0 | 2.0 | 2.0 |
| DMDM Hydantoin and Iodopropynyl Butylcarbamate | Preservative | 0.6 | 0.6 | 0.6 |
| Citric Acid (50%) | Neutralizer | qs to pH 7 | qs to pH 7 | qs to pH 7 |
| TOTAL | | 100 | 100 | 100 |

Formula 5 is similar to Formula 1 with the exception that Formula 5 has been altered to have organic UV filters only (i.e., no inorganic sunscreen actives or agents). Formulation 5 was prepared to understand the suspension mechanism (as there is nothing to suspend in this formulation), with the difference in weight from Formula 1 made up with water.

Formula 6 is similar to Formula 1 with the exception that Formula 6 has been altered to have inorganic UV filters only (i.e., no organic sunscreen actives or agents). Formulation 6 was prepared to determine if organic UV filters are required to see the SPF boost, with difference in weight from Formula 1 made up with solubilizers of similar polarity to the organic UV filters. These solubilizers are listed as caprylic/capric triglyceride (commercially available as Myritol 318) and isopropyl myristate (commercially available as Liponate IPM).

Formula 7 is the same formulation as Formula 6 with the exception that the heat treated xanthan gum is replaced with non-heat treated xanthan gum as a control.

The following results were determined—

TABLE 2

SPF Values

| | Pre-immersion (static) SPF value | Post 80-minute immersion SPF Value |
|---|---|---|
| Formula 5 | 18.5 | 5.8 |
| Formula 6 | 9.2 | 9.5 |
| Formula 7 | 10.2 | 3.4 |

A lack of inorganic UV filters in Formula 5 results in a reduction in the static SPF value. Based on the 80-minute immersion SPF value, it appears that the mechanism for SPF boost may be suspension of the inorganic particulate sunscreens, as this formulation has no particulates to suspend and subsequently shows no SPF boost and limited retention of organic UV filters. Formula 6 contains only inorganic UV filters and exhibits approximately 100% SPF retention after 80 minutes. Formula 7, which differs from Formula 6 in that it utilizes traditional (non-heat treated) xanthan gum, does not provide the improvement in SPF retention that Formula 6 gives.

Example 3

Polymers

Two additional formulations were made to test the scope of the film-forming polymer chemistry needed to realize the SPF boost. In addition to Formula 1, which utilizes polyacrylate chemistry, a formulation with PVP/Eicosene Copolymer (oil dispersible polymer) was made as well as one with polyurethane chemistry (water dispersible polymer) for comparison.

The two sunscreen formulations were prepared as follows—

| Ingredient | Function | Formula 8 | Formula 9 |
|---|---|---|---|
| PHASE A | | | |
| Isohexadecane | Emollient | 1.5 | 1.5 |
| C12-C15 alkyl benzoate | Emollient | 3.0 | 3.0 |
| Cyclopentasiloxane | Emollient | 2.25 | 2.25 |
| Sorbitan Stearate | Emulsifier | 1.0 | 1.0 |
| Glyceryl Stearate (and) PEG-100 Stearate | Emulsifier | 2.0 | 2.0 |
| Octocrylene | UVB filter | 2.0 | 2.0 |
| Ethylhexyl Methoxycinnamate | UVB filter | 7.5 | 7.5 |
| Benzophenone-3 | UVB filter | 3.0 | 3.0 |
| ZnO (and) C12-C15 Alkyl Benzoate (and) Polyhydroxystearic Acid | UVA/B filter | 6.0 | 6.0 |
| PVP/Eicosene Copolymer | Film former | 2.0 | 0.0 |
| PHASE B | | | |
| Water | | 56.65 | 53.39 |
| Dehydroxanthan Gum | Suspension agent, Rheology modifier | 0.5 | 0.5 |
| Xanthan Gum | Rheology modifier | 0.0 | 0.0 |
| Acrylates Copolymer | Film former | 0.0 | 0.0 |
| Glycerin | Humectant | 3.0 | 3.0 |

-continued

| Ingredient | Function | Formula 8 | Formula 9 |
|---|---|---|---|
| TiO$_2$ and Alumina and Silica and Sodium Polyacrylate | UVB filter | 7.0 | 7.0 |
| PPG-17/IPDI/DMPA Copolymer | Film Former | 0.0 | 5.26 |
| PHASE C | | | |
| Corn Starch Modified | Aesthetic enhancer | 2.0 | 2.0 |
| DMDM Hydantoin and Iodopropynyl Butylcarbamate | Preservative | 0.6 | 0.6 |
| Citric Acid (50%) | Neutralizer | qs to pH 7 | qs to pH 7 |
| TOTAL | | 100 | 100 |

The resulting SPF values were as follows—

TABLE 3

| SPF Values | | |
|---|---|---|
| | Pre-immersion (static) SPF value | Post-immersion (80 min) SPF Value |
| Formula 1 | 47.9 | 32.6 |
| Formula 8 | 52.9 | 5.8 |
| Formula 9 | 50.6 | 28.5 |

From the above results it is seen that there should be at least one film-forming polymer present in the water phase that is either water dispersible or water soluble in order to provide a boost in SPF. The PVP/Eicosene copolymer, which resides in the oil phase of Formula 8, does not appear to contribute here in the boost or retention of SPF.

Example 4

Formula 10 below is a formulation where ZnO is present in the water phase and TiO$_2$ is present in the oil phase:

| Ingredient | Function | Formula 10 |
|---|---|---|
| PHASE A | | |
| Isohexadecane | Emollient | 1.5 |
| C12-C15 alkyl benzoate | Emollient | 3.0 |
| Cyclopentasiloxane | Emollient | 2.25 |
| Sorbitan Stearate | Emulsifier | 1.0 |
| Glyceryl Stearate (and) PEG-100 Stearate | Emulsifier | 2.0 |
| Octocrylene | UVB filter | 2.0 |
| Ethylhexyl Methoxycinnamate | UVB filter | 7.5 |
| Benzophenone-3 | UVB filter | 3.0 |
| C12-C15 Alkyl Benzoate (and) TiO$_2$ (and) Polyhydroxystearic Acid (and) Aluminum Stearate (and) Alumina | UVB filter | 10.0 |
| PHASE B | | |
| Water | | 52.25 |
| Dehydroxanthan Gum | Suspension agent, Rheology modifier | 0.5 |
| Acrylates Copolymer | Film former | 4.4 |
| Glycerin | Humectant | 3.0 |
| Zinc Oxide | UVA/B filter | 5.0 |

| Ingredient | Function | Formula 10 |
|---|---|---|
| PHASE C | | |
| Corn Starch Modified | Aesthetic enhancer | 2.0 |
| DMDM Hydantoin and Iodopropynyl Butylcarbamate | Preservative | 0.6 |
| Citric Acid (50%) | Neutralizer | qs to pH 7 |
| TOTAL | | 100 |

Example 5

Formula 11 below is a sunless tanning formulation with UV filter:

| Ingredient | Function | Formula 11 |
|---|---|---|
| PHASE A | | |
| Glycerol Monostearate | Emulsifier | 2.0 |
| PEG-100 Stearate | Emulsifier | 1.0 |
| Coco-Caprylate/Caprate | Emollient | 5.0 |
| Cetyl Alcohol | Emulsifier | 2.0 |
| Dioctyl Adipate | Emollient | 3.0 |
| Cetearyl Alcohol | Emulsifier | 1.0 |
| Octyl Palmitate | Emollient | 3.0 |
| Sorbitan Palmitate | Emollient | 0.5 |
| Dimethicone | Emollient | 0.5 |
| Myristyl Myristate | Emollient | 1.0 |
| Ethylhexyl Methoxycinnamate | UVB filter | 7.5 |
| PHASE B | | |
| Water | | 47.55 |
| Dehydroxanthan Gum | Suspension agent, Rheology modifier | 0.5 |
| Propylene Glycol | Humectant | 3.0 |
| Disodium EDTA | Chelating agent | 0.05 |
| Acrylates Copolymer | Film Former | 4.4 |
| PHASE C | | |
| Water | | 5.0 |
| Dihydroxyacetone | Self tanning agent | 5.0 |
| PHASE D | | |
| Corn Starch Modified | UV Filter | 5.0 |
| Mica | Inorganic particulate | 2.0 |
| Phenoxyethanol (and) Methylparaben (and) Ethylparaben (and) Butylparaben (and) Propylparaben (and) Isobutylparaben | Preservative | 1.0 |
| Citric Acid (50%) | | qs to pH 4.5 |
| TOTAL | | 100 |

Example 6

Formula 12 below is a spray sunscreen formulation:

| Ingredient | Function | Formula 12 |
|---|---|---|
| PHASE A | | |
| Isohexadecane | Emollient | 1.5 |
| C12-C15 alkyl benzoate | Emollient | 3.0 |
| Cyclopentasiloxane | Emollient | 2.25 |
| Sorbitan Stearate | Emulsifier | 1.0 |
| Glyceryl Stearate (and) PEG-100 Stearate | Emulsifier | 2.0 |
| Octocrylene | UVB filter | 2.0 |
| Ethylhexyl Methoxycinnamate | UVB filter | 7.5 |
| Benzophenone-3 | UVB filter | 3.0 |
| ZnO (and) C12-C15 Alkyl Benzoate (and) Polyhydroxystearic Acid | UVA/B filter | 6.0 |
| PHASE B | | |
| Water | | 54.7 |
| Dehydroxanthan Gum | Suspension agent, Rheology modifier | 0.05 |
| Acrylates Copolymer | Film former | 4.4 |
| Glycerin | Humectant | 3.0 |
| TiO$_2$ and Alumina and Silica and Sodium Polyacrylate | UVB filter | 7.0 |
| PHASE C | | |
| Corn Starch Modified | Aesthetic enhancer | 2.0 |
| DMDM Hydantoin and Iodopropynyl Butylcarbamate | Preservative | 0.6 |
| Citric Acid (50%) | Neutralizer | qs to pH 7 |
| TOTAL | | 100 |

Example 7

Formula 13 below is a whitening formulation with sunscreen actives:

| Ingredient | Function | Formula 13 |
|---|---|---|
| PHASE A | | |
| Isohexadecane | Emollient | 1.5 |
| C12-C15 alkyl benzoate | Emollient | 3.0 |
| Cyclopentasiloxane | Emollient | 2.25 |
| Sorbitan Stearate | Emulsifier | 1.0 |
| Glyceryl Stearate (and) PEG-100 Stearate | Emulsifier | 2.0 |
| Octocrylene | UVB filter | 2.0 |
| Ethylhexyl Methoxycinnamate | UVB filter | 7.5 |
| Benzophenone-3 | UVB filter | 3.0 |
| PHASE B | | |
| Water | | 55.25 |
| Dehydroxanthan Gum | Suspension agent, Rheology modifier | 0.5 |
| Acrylates Copolymer | Film former | 4.4 |
| Glycerin | Humectant | 3.0 |
| PHASE C | | |
| Hydroquinone | Whitening agent | 2.0 |
| Water | | 10.0 |
| PHASE D | | |
| Corn Starch Modified | UV Filter | 2.0 |
| DMDM Hydantoin and Iodopropynyl Butylcarbamate | Preservative | 0.6 |
| TOTAL | | 100 |

Example 8

Formula 14 below is a whitening formulation with particulates:

| Ingredient | Function | Formula 14 |
|---|---|---|
| PHASE A | | |
| Steareth-21 | Emulsifier | 3.0 |
| Steareth-2 | Emulsifier | 1.0 |
| Stearic Acid | Emulsifier | 4.0 |
| Butyl Methoxydibenzoylmethane | UVA/B filter | 2.0 |
| Ethylhexyl Methoxycinnamate | UVB filter | 7.5 |
| Dimethicone | Emollient | 1.0 |
| Cyclomethicone | Emollient | 3.0 |
| PHASE B | | |
| Disodium EDTA | Chelating agent | 0.1 |
| Water | | 55.4 |
| Glycerin | Humectant | 3.5 |
| Dehydroxanthan Gum | Suspension Agent, Rheology Modifier | 0.5 |
| Acrylates Copolymer | Film former | 4.4 |
| PHASE C | | |
| Propylene Glycol | Humectant | 2.0 |
| Corn Starch Modified | UV Filter | 2.0 |
| Talc | Whitening Particulate | 10.0 |
| DMDM Hydantoin and Iodopropynyl Butylcarbamate | Preservative | 0.6 |
| TOTAL | | 100 |

Example 9

The following formulation was made to investigate the water resistance potential of a formulation containing only inorganic UV sunscreens (Formula 15). The concentration of the inorganic UV filters was increased to maintain similar SPF values. SPF values provided in Table 4 below were measured using the same procedure described previously from an outside laboratory.

Inorganic only UV Filter Sunscreen

| Ingredient | Function | Formula 15 |
|---|---|---|
| PHASE A | | |
| Isohexadecane | Emollient | 1.5 |
| C12-C15 alkyl benzoate | Emollient | 3.0 |
| Cyclopentasiloxane | Emollient | 2.25 |
| Sorbitan Stearate | Emulsifier | 1.0 |

-continued

| Ingredient | Function | Formula 15 |
|---|---|---|
| Glyceryl Stearate (and) PEG-100 Stearate | Emulsifier | 2.0 |
| ZnO (and) C12-C15 Alkyl Benzoate (and) Polyhydroxystearic Acid | UVA/B filter | 20.0 |
| PHASE B | | |
| Water | | 38.75 |
| Dehydroxanthan Gum | Suspension agent, Rheology modifier | 0.5 |
| Acrylates Copolymer | Film former | 4.4 |
| Glycerin | Humectant | 3.0 |
| TiO₂ and Alumina and Silica and Sodium Polyacrylate | UVB filter | 23.0 |
| PHASE C | | |
| DMDM Hydantoin and Iodopropynyl Butylcarbamate | Preservative | 0.6 |
| Citric Acid (50%) | Neutralizer | qs to pH 7 |
| TOTAL | | 100 |

Example 10

The following formulation was made to investigate the use of Acrylates/Octylacrylamide Copolymer in this formulation. Similar results (see Table 4) were achieved using this polymer (Formula 16), using the same in-vitro SPF procedure previously described.

Sunscreen Formulation

| Ingredient | Function | Formula 16 |
|---|---|---|
| PHASE A | | |
| Isohexadecane | Emollient | 1.5 |
| C12-C15 alkyl benzoate | Emollient | 3.0 |
| Cyclopentasiloxane | Emollient | 2.25 |
| Sorbitan Stearate | Emulsifier | 1.0 |
| Glyceryl Stearate (and) PEG-100 Stearate | Emulsifier | 2.0 |
| Octocrylene | UVB filter | 2.0 |
| Ethylhexyl Methoxycinnamate | UVB filter | 7.5 |
| Benzophenone-3 | UVB filter | 3.0 |
| ZnO (and) C12-C15 Alkyl Benzoate (and) Polyhydroxystearic Acid | UVA/B filter | 6.0 |
| PHASE B | | |
| Water | | 53.34 |
| Dehydroxanthan Gum | Suspension agent, Rheology modifier | 0.70 |
| Acrylates/Octylacrylamide Copolymer | Film former | 2.0 |
| Glycerin | Humectant | 3.0 |
| TiO₂ and Alumina and Silica and Sodium Polyacrylate | UVB filter | 7.0 |
| Triethanolamine | Neutralizer | 0.71 |
| PHASE C | | |
| Aluminum Starch Octenylsuccinate | Aesthetic enhancer | 2.0 |
| DMDM Hydantoin and Iodopropynyl Butylcarbamate | Preservative | 0.6 |

-continued

| Ingredient | Function | Formula 16 |
|---|---|---|
| Citric Acid (50%) | Neutralizer | qs to pH 7 |
| TOTAL | | 100 |

TABLE 4

| | SPF Values | |
|---|---|---|
| In-vitro Data | Formulation 15 | Formulation 16 |
| Pre-immersion SPF | 48.8 | 46.8 |
| Post-immersion SPF | 48.7 | 36.6 |

Example 11

In Vivo Evaluation

Following FDA Final Monograph test methodology for Very Water Resistant SPF, the non-randomized study was conducted as a blind evaluation on 5 healthy male/female volunteers with skin types I, II, and/or III. A timed series of 5 UV doses increasing in 25% increments was administered to the mid-back. The solar simulator used provides UV radiation between 290-400 nm, which is similar to sunlight at sea level. Subjects returned to the laboratory 22-24 hours later and a trained evaluator graded responses of the UV exposed sites on a scale of 0 to 7. This grading produced the initial Minimum Erythema Dose ('MED'). This initial MED is defined as the lowest UV dose that produces a response grade of 2 (mild erythema reaching the borders of the exposed site) or higher.

Adjacent 50 cm² rectangles were drawn on the subject's back. 100 mg of test product was applied in the designated rectangle and 100 mg of the 8% Homosalate control was applied in the remaining rectangle. Products were applied by "spotting" the material across the area and gently spreading until a uniform film was applied to the entire area. After 15 minutes post application, the subject was immersed to the upper back in gently moving water that was maintained at 23-32° C. The subject remained in the water for 20 minutes followed by a 20 minute drying period. This was repeated for a total of 80 minutes immersion.

After the last water immersion, 100 mg of the 8% Homosalate standard was re-applied and a series of 7 progressively increasing timed UV doses were given to the site with the test product applied. 15 minutes post application of the 8% Homosalate standard, the 7 UV doses were also given. 5 UV doses to an untreated area of the back, increasing by 25% increments, was also given for repeat MED determination, called final MED.

22-24 hours after UV exposure, the subject returned and was again evaluated. SPF was computed as a ratio of MED for the site treated with product versus MED of untreated skin. Static SPF value was reported as ratio of MED for the site treated with product versus final MED. The results were as follows—

TABLE 5 in vivo SPF Results

| In-vivo Data | Formulation 1 with heat treated xanthan and film former | Formulation 3 with only heat treated xanthan | Formulation 2 with regular xanthan and film former |
|---|---|---|---|
| Pre 80-minute immersion SPF | 29 | 10 | 19 |
| Post 80-minute immersion SPF | 27 | 9 | 19 |

Example 12

In Vivo Evaluation

Following the same FDA Final Monograph test methodology for Very Water Resistant SPF as listed in the previous example, exception being the non-randomized study was conducted as a blind evaluation on 3 healthy male/female volunteers. Formulation 15, containing heat treated xanthan gum and film former with only inorganic UV filters was tested.

SPF was again computed as a ratio of MED for the site treated with product versus MED of untreated skin. Static SPF value was reported as ratio of MED for the site treated with product versus final MED. The results were as follows—

TABLE 6 in vivo SPF Result

| In-vivo Data | Formulation 15 with heat treated xanthan and film former |
|---|---|
| Pre 80-minute immersion SPF | 23.9 |
| Post 80-minute immersion SPF | 22.8 |

Although the present invention has been described and illustrated in detail, it is to be understood that the same is by way of illustration and example only, and is not to be taken as a limitation. The spirit and scope of the present invention are to be limited only by the terms of any claims presented hereafter.

What is claimed is:
1. Sunscreen composition comprising:
one or more sunscreen actives, wherein the one or more sunscreen actives comprises at least one inorganic sunscreen active;
one or more film forming polymers; and
dehydroxanthan gum,
wherein at least one film-forming polymer is present in the water phase of the composition, and
wherein the combination of the dehydroxanthan gum and one or more film forming polymers result in an SPF enhancement after water immersion.
2. Sunscreen composition according to claim 1 wherein the one or more sunscreen actives are present in an amount of about 0.25 to about 30% by weight, based on total weight of the composition.
3. Sunscreen composition according to claim 1 wherein the one or more film forming polymers are present in an amount of about 0.05 to about 10% by weight, based on total weight of the composition.
4. Sunscreen composition according to claim 1 wherein the heat treated dehydroxanthan gum is present in an amount of about 0.05 to about 20% by weight, based on total weight of the composition.
5. Sunscreen composition according to claim 1 wherein the one or more inorganic sunscreen actives comprises at least zinc oxide and/or titanium dioxide.
6. Sunscreen composition according to claim 1 wherein at least one of the one or more inorganic sunscreen actives is in a water phase of the composition.
7. Sunscreen composition according to claim 1 wherein the one or more film forming polymers comprises at least an acrylates copolymer.
8. Sunscreen composition according to claim 1 wherein the one or more film forming polymers comprises at least a polyurethane copolymer.
9. Sunscreen composition according to claim 1 wherein the composition is an oil-in-water emulsion.
10. Sunscreen composition according to claim 1 wherein the one or more sunscreen actives comprises at least one or more particulates chosen from clays, agars, guars, nanoparticles, native and modified starches, modified cellulosics, zinc oxide, titanium dioxide and combinations thereof.
11. Sunscreen composition according to claim 10 wherein the modified starches comprises at least an octenyl succinate (OSA) modified starch, modified corn starch and combinations thereof.
12. Sunscreen composition according to claim 1 wherein the one or more sunscreen actives comprises at least one organic sunscreen active.
13. Sunscreen composition according to claim 12 wherein the at least one organic sunscreen active is selected from the group consisting of ethylhexyl methoxycinnamate (octinoxate), ethylhexyl salicylate (octisalate), butylmethoxydibenzoylmethane, methoxydibenzoylmethane, avobenzone, benzophenone-3 (oxybenzone), octocrylene, aminobenzoic acid, cinoxate, dioxybenzone, homosalate, menthyl anthranilate, octocrylene, octisalate, oxybenzone, padimate O, phenylbenzimidazole sulfonic acid, sulisobenzone, trolamine salicylate and combinations thereof.
14. Sunscreen composition according to claim 1 further comprising one or more active agents.
15. Sunscreen composition according to claim 14 wherein the active agents are selected from the group consisting of anti-acne agents, antimicrobial agents, anti-inflammatory agents, analgesics, anti-erythemal agents, antiruritic agents, antiedemal agents, antipsoriatic agents, antifungal agents, skin protectants, vitamins, antioxidants, scavengers, antiirritants, antibacterial agents, antiviral agents, antiaging agents, protoprotection agents, hair growth enhancers, hair growth inhibitors, hair removal agents, antidandruff agents, anti-seborrheic agents, exfoliating agents, wound healing agents, anti-ectoparacitic agents, sebum modulators, immunomodulators, hormones, botanicals, moisturizers, astringents, cleansers, sensates, antibiotics, anesthetics, steroids, tissue healing substances, tissue regenerating substances, amino acids, peptides, minerals, ceramides, hydroxyalkyl urea, biohyaluronic acids, vitamins, skin lightening agents, self tanning agents, coenzyme Q10, niacinimide, capcasin, caffeine, and combinations thereof.
16. Sunscreen composition according to claim 1 further comprising one or more adjuvants.
17. Sunscreen composition according to claim 1 further comprising one or more conditioning agents.
18. Sunscreen composition according to claim 1 further comprising one or more preservatives.

19. Sunscreen composition according to claim 1 further comprising one or more aesthetic enhancers.

20. Sunscreen composition according to claim 19 wherein the one or more aesthetic enhancers is selected from the group consisting of corn starch, tapioca starch and combinations thereof.

21. Method of reducing UV radiation on a substrate comprising applying to the substrate an effective amount of the sunscreen composition according to claim 1.

22. Sunscreen composition according to claim 1 wherein the dehydroxanthan gum has a moisture content of less than about 8%.

\* \* \* \* \*